(12) United States Patent
Waters et al.

(10) Patent No.: US 10,909,661 B2
(45) Date of Patent: Feb. 2, 2021

(54) SYSTEMS AND METHODS TO REDUCE NEAR-FIELD ARTIFACTS

(71) Applicant: ACIST Medical Systems, Inc., Eden Prairie, MN (US)

(72) Inventors: Kendall R. Waters, Livermore, CA (US); Joseph A. Jamello, Saratoga, CA (US)

(73) Assignee: ACIST MEDICAL SYSTEMS, INC., Eden Prairie, MN (US)

(*) Notice: Subject to any disclaimer, the term of this patent is extended or adjusted under 35 U.S.C. 154(b) by 0 days.

(21) Appl. No.: 14/878,288

(22) Filed: Oct. 8, 2015

(65) Prior Publication Data

US 2017/0103498 A1   Apr. 13, 2017

(51) Int. Cl.
*G06K 9/40* (2006.01)
*G06T 5/00* (2006.01)
(Continued)

(52) U.S. Cl.
CPC .............. *G06T 5/001* (2013.01); *A61B 5/004* (2013.01); *A61B 5/0066* (2013.01); (Continued)

(58) Field of Classification Search
CPC ... G06K 9/36; G06K 9/40; G06T 5/00; G06T 5/001; G06T 5/002; G06T 5/003; G06T 5/004; G06T 5/10; G06T 5/20; G06T 5/50; G06T 11/008; G06T 11/003; G06T 2207/10101; G06T 2207/10132; G06T 2207/30101; A61B 5/0033; A61B 5/0035; A61B 5/0044; A61B 5/0066; A61B 5/0073; A61B 5/0084; A61B 5/02007; A61B 5/027; A61B 5/145; A61B 5/14503; A61B 5/6852; A61B 5/7203; A61B 5/7217; A61B 5/725; A61B 6/5258; A61B 7/005; A61B 8/12; A61B 8/481; A61B 8/483; A61B 8/52; A61B 8/5207; A61B 8/5269;
(Continued)

(56) References Cited

U.S. PATENT DOCUMENTS 3,918,025 A   11/1975   Koshikawa et al.
4,347,443 A   8/1982    Whitney
(Continued)

FOREIGN PATENT DOCUMENTS

CN   101208045 A   6/2008
CN   103025247 A   4/2013
(Continued)

OTHER PUBLICATIONS

Dumane et al., "Use of Frequency Diversity and Nakagami Statistics in Ultrasonic Tissue Characterization," IEEE Transactions on Ultrasonics, Ferroelectrics, and Frequency Control, vol. 48, No. 5, Sep. 2001, pp. 1139-1146.
(Continued)

*Primary Examiner* — Eric Rush
(74) *Attorney, Agent, or Firm* — Fredrikson & Byron, P, A,

(57) ABSTRACT

Systems and methods to reduce near-field artifacts from intravascular images. Disclosed systems and methods are adapted to automatically identify near-field image artifacts in imaging data and generate an enhanced intravascular image by reducing near-field image artifacts.

21 Claims, 10 Drawing Sheets

(51) Int. Cl.
  *A61B 8/08* (2006.01)
  *A61B 5/00* (2006.01)
  *A61B 8/12* (2006.01)
  *G06T 11/00* (2006.01)
  *G06T 5/50* (2006.01)
  *A61B 8/00* (2006.01)
  *G06T 5/20* (2006.01)
  *G06T 7/00* (2017.01)
  *A61B 5/02* (2006.01)

(52) U.S. Cl.
  CPC .......... *A61B 5/7217* (2013.01); *A61B 8/0891* (2013.01); *A61B 8/12* (2013.01); *A61B 8/445* (2013.01); *A61B 8/5269* (2013.01); *G06K 9/40* (2013.01); *G06T 5/20* (2013.01); *G06T 5/50* (2013.01); *G06T 7/0012* (2013.01); *G06T 11/003* (2013.01); *G06T 11/008* (2013.01); *A61B 5/0084* (2013.01); *A61B 5/02007* (2013.01); *A61B 5/7207* (2013.01); *A61B 5/7225* (2013.01); *A61B 2576/02* (2013.01); *G06T 2207/10101* (2013.01); *G06T 2207/10132* (2013.01); *G06T 2207/30101* (2013.01)

(58) Field of Classification Search
  CPC ..... A61B 5/004; A61B 5/7207; A61B 5/7225; A61B 8/445; A61B 2576/02; G16H 30/40
  USPC ........ 382/128, 130–132, 254, 260, 263–265, 382/275, 282; 600/121, 122, 160, 505
  See application file for complete search history.

(56) References Cited

U.S. PATENT DOCUMENTS

| | | | |
|---|---|---|---|
| 4,850,363 A | 7/1989 | Yanagawa | |
| 4,860,758 A | 8/1989 | Yanagawa et al. | |
| 4,949,310 A | 8/1990 | Smith et al. | |
| 5,070,734 A | 12/1991 | Kawabuchi et al. | |
| 5,070,735 A | 12/1991 | Reichert et al. | |
| 5,131,396 A | 7/1992 | Ishiguro et al. | |
| 5,183,048 A * | 2/1993 | Eberle | A61B 8/12 600/447 |
| 5,203,338 A | 4/1993 | Jang | |
| 5,361,767 A | 11/1994 | Yukov | |
| 5,363,849 A | 11/1994 | Suorsa et al. | |
| 5,396,285 A | 3/1995 | Hedberg et al. | |
| 5,462,057 A | 10/1995 | Hunt et al. | |
| 5,531,679 A | 7/1996 | Schulman et al. | |
| 5,690,115 A | 11/1997 | Feldman et al. | |
| 5,741,552 A | 4/1998 | Takayama et al. | |
| 5,795,296 A * | 8/1998 | Pathak | A61B 5/1075 600/443 |
| 5,833,615 A | 11/1998 | Wu et al. | |
| 5,848,969 A | 12/1998 | Panescu et al. | |
| 5,876,343 A | 3/1999 | Teo et al. | |
| 5,921,931 A * | 7/1999 | O'Donnell | A61B 8/06 382/162 |
| 6,015,385 A * | 1/2000 | Finger | G01S 7/52046 600/443 |
| 6,036,650 A * | 3/2000 | Wu | A61B 8/12 600/447 |
| 6,132,374 A | 10/2000 | Hossack et al. | |
| 6,139,501 A | 10/2000 | Roundhill et al. | |
| 6,154,572 A | 11/2000 | Chaddha | |
| 6,216,025 B1 | 4/2001 | Kruger | |
| 6,277,075 B1 | 8/2001 | Torp et al. | |
| 6,589,181 B2 * | 7/2003 | Grunwald | A61B 8/00 600/437 |
| 6,645,147 B1 | 11/2003 | Jackson et al. | |
| 7,194,294 B2 | 3/2007 | Panescu et al. | |
| 7,691,061 B2 | 4/2010 | Hirota | |
| 7,925,064 B2 | 4/2011 | Cloutier et al. | |
| 9,292,918 B2 * | 3/2016 | Zagrodsky | G06T 7/33 |
| 9,761,006 B2 | 9/2017 | Bergner et al. | |
| 9,858,668 B2 * | 1/2018 | Jones | G06T 7/0016 |
| 10,089,755 B2 * | 10/2018 | Griffin | G06T 7/194 |
| 2001/0017941 A1 | 8/2001 | Chaddha | |
| 2001/0029336 A1 | 10/2001 | Teo | |
| 2003/0063787 A1 | 4/2003 | Natanzon et al. | |
| 2003/0078497 A1 | 4/2003 | Ji et al. | |
| 2003/0097069 A1 | 5/2003 | Avinash et al. | |
| 2003/0103212 A1 * | 6/2003 | Westphal | A61B 5/0064 356/479 |
| 2003/0191392 A1 | 10/2003 | Haldeman | |
| 2003/0208123 A1 | 11/2003 | Panescu | |
| 2004/0030250 A1 | 2/2004 | Stewart | |
| 2004/0037164 A1 | 2/2004 | Garlick et al. | |
| 2004/0199047 A1 | 10/2004 | Taimisto et al. | |
| 2005/0119573 A1 | 6/2005 | Vilenkin et al. | |
| 2005/0215897 A1 | 9/2005 | Sakaguchi et al. | |
| 2005/0249391 A1 | 11/2005 | Kimmel et al. | |
| 2006/0253028 A1 | 11/2006 | Lam et al. | |
| 2007/0016068 A1 | 1/2007 | Grunwald et al. | |
| 2007/0036404 A1 | 2/2007 | Li | |
| 2007/0167710 A1 * | 7/2007 | Unal | A61B 5/0066 600/407 |
| 2007/0201736 A1 * | 8/2007 | Klingensmith | A61B 5/02007 382/128 |
| 2008/0015569 A1 | 1/2008 | Saadat et al. | |
| 2008/0031498 A1 | 2/2008 | Corcoran et al. | |
| 2008/0043024 A1 * | 2/2008 | Schiwietz | G06T 11/006 345/442 |
| 2008/0075375 A1 * | 3/2008 | Unal | G06K 9/621 382/243 |
| 2008/0200815 A1 | 8/2008 | Van Der Steen et al. | |
| 2008/0234582 A1 * | 9/2008 | Nair | A61B 5/02007 600/443 |
| 2009/0088830 A1 | 4/2009 | Mohamed et al. | |
| 2009/0284332 A1 | 11/2009 | Moore et al. | |
| 2010/0010344 A1 * | 1/2010 | Ahn | A61B 8/483 382/131 |
| 2010/0094127 A1 * | 4/2010 | Xu | G06T 7/0042 382/131 |
| 2010/0174190 A1 | 7/2010 | Hancock et al. | |
| 2010/0312092 A1 | 12/2010 | Listz et al. | |
| 2010/0312109 A1 | 12/2010 | Satoh | |
| 2011/0071404 A1 * | 3/2011 | Schmitt | G06T 7/0012 382/128 |
| 2011/0160586 A1 | 6/2011 | Li et al. | |
| 2011/0196237 A1 | 8/2011 | Pelissier et al. | |
| 2011/0257527 A1 | 10/2011 | Suri | |
| 2012/0022360 A1 | 1/2012 | Kemp | |
| 2012/0065511 A1 | 3/2012 | Jamello, III | |
| 2012/0123271 A1 | 5/2012 | Cai | |
| 2012/0170848 A1 * | 7/2012 | Kemp | G06T 7/0012 382/275 |
| 2012/0224751 A1 * | 9/2012 | Kemp | G01B 9/02057 382/128 |
| 2013/0109968 A1 | 5/2013 | Azuma | |
| 2013/0303907 A1 | 11/2013 | Corl | |
| 2013/0303910 A1 | 11/2013 | Hubbard et al. | |
| 2013/0317359 A1 | 11/2013 | Wilson et al. | |
| 2014/0099011 A1 * | 4/2014 | Begin | G06T 7/0012 382/131 |
| 2014/0100440 A1 * | 4/2014 | Cheline | G06T 7/13 600/407 |
| 2014/0180078 A1 | 6/2014 | Nair | |
| 2014/0180083 A1 | 6/2014 | Hoseit | |
| 2014/0180108 A1 | 6/2014 | Rice | |
| 2014/0257087 A1 * | 9/2014 | Elbasiony | A61B 5/061 600/424 |
| 2014/0268167 A1 | 9/2014 | Friedman et al. | |
| 2014/0270445 A1 * | 9/2014 | Kemp | A61B 5/6852 382/131 |
| 2014/0276065 A1 | 9/2014 | He et al. | |
| 2014/0316758 A1 | 10/2014 | Yagi et al. | |
| 2014/0350404 A1 | 11/2014 | Nikhil et al. | |
| 2015/0099975 A1 | 4/2015 | Lam et al. | |
| 2015/0141832 A1 | 5/2015 | Yu et al. | |
| 2015/0245776 A1 | 9/2015 | Hirohata et al. | |

(56) References Cited

U.S. PATENT DOCUMENTS

| | | |
|---|---|---|
| 2015/0356734 A1 | 12/2015 | Ooga et al. |
| 2016/0007967 A1 | 1/2016 | Johnson et al. |
| 2016/0022248 A1 | 1/2016 | Mori et al. |
| 2016/0206290 A1* | 7/2016 | Itoh .................. A61B 8/461 |
| 2017/0035394 A1 | 2/2017 | Maeda |
| 2017/0100100 A1 | 4/2017 | Jamello et al. |
| 2017/0193658 A1 | 7/2017 | Cardinal et al. |
| 2017/0224286 A1* | 8/2017 | Sakamoto ............ A61B 5/7203 |
| 2017/0301089 A1 | 10/2017 | Lam et al. |
| 2017/0330331 A1 | 11/2017 | Bhatt et al. |
| 2018/0042575 A1 | 2/2018 | Moore et al. |

FOREIGN PATENT DOCUMENTS

| | | |
|---|---|---|
| EP | 346889 A1 | 1/1995 |
| EP | 851241 A2 | 7/1998 |
| EP | 1387317 A1 | 2/2004 |
| EP | 1609423 A2 | 12/2005 |
| EP | 1988505 A1 | 11/2008 |
| EP | 2488107 A2 | 8/2012 |
| JP | 62221335 A | 9/1987 |
| JP | H09000522 A | 1/1997 |
| JP | 2001333902 A | 12/2001 |
| JP | 2002530143 A | 9/2002 |
| JP | 2004180784 A | 7/2004 |
| JP | 2006014938 A | 1/2006 |
| JP | 2007029520 A | 2/2007 |
| JP | 2007229015 A | 9/2007 |
| JP | 2008508970 A | 3/2008 |
| JP | 2008536638 A | 9/2008 |
| JP | 2009545406 A | 12/2009 |
| JP | 4648652 B2 | 3/2011 |
| JP | 2013507227 A | 3/2013 |
| JP | 2015104463 A | 6/2015 |
| WO | 0101864 A1 | 1/2001 |
| WO | 2006015877 A1 | 2/2006 |
| WO | 2006102511 A2 | 9/2006 |
| WO | 2006113857 A1 | 10/2006 |
| WO | 2006122001 A2 | 11/2006 |
| WO | 2007098209 A2 | 8/2007 |
| WO | 2008016992 A1 | 2/2008 |
| WO | 2008110013 A1 | 9/2008 |
| WO | 2011046903 A1 | 4/2011 |
| WO | 2014186268 A1 | 11/2014 |
| WO | 2017100274 A1 | 6/2017 |

OTHER PUBLICATIONS

Foster, "Transducer Materials and Probe Construction," Ultrasound in Medicine and Biology, vol. 26, Supp. 1, 2000, pp. S2-55.

Frijlink et al., "High Frequency Harmonic Imaging in Presence of Intravascular Stents," IEEE Ultrasonics Symposium, 2003, pp. 208-211.

Garcia-Garcia et al., "Imaging of coronary atherosclerosis: intravascular ultrasound," European Heart Journal, vol. 3, 2010, pp. 2456-2469.

Seo et al., "Sidelobe Suppression in Ultrasound Imaging Using Dual Apodization with Cross-Correlation," IEEE Transactions on Ultrasonics, Ferroelectrics, and Frequency Control, vol. 55, No. 10, Oct. 2008, pp. 2198-2210.

Shankar et al., "Computer-Aided Classification of Breast Masses in Ultrasonic B-Scans Using a Multiparameter Approach," IEEE Transactions on Ultrasonics, Ferroelectrics, and Frequency Control, vol. 50, No. 8, Aug. 2003, pp. 1002-1009.

Smith et al., "The Maltese Cross Processor: Speckle Reduction for Circular Transducers," Ultrasonic Imaging, vol. 10, No. 3, Jul. 1988, pp. 153-170.

U.S. Appl. No. 61/218,177, titled Vector Domain Image Enhancement for Mechanically Rotating Imaging Catheters, filed Jun. 18, 2009.

Van Der Steen et al., "IVUS Harmonic Imaging," Ultrasound in Medicine and Biology, vol. 26, Supp. 2, 2000, p. A90.

Wang et al., "Optimizing the Beam Pattern of a Forward-Viewing Ring-Annular Ultrasound Array for Intravascular Imaging," IEEE Transactions on Ultrasonics, Ferroelectrics, and Frequency Control, vol. 49, No. 12, Dec. 2002, pp. 1652-1664.

Waters et al., "Development of a High-Definition Intravascular Ultrasound Imaging System and Catheter," IEEE International Ultrasonics Symposium Proceedings, Oct. 18, 2011, 4 pages.

International Patent Application No. PCT/US2016/054589, International Search Report & Written Opinion dated Dec. 16, 2016, 15 pages.

Moore et al., "Intravascular Ultrasound Image Processing of Blood-Filled or Blood-Displaced Lumens," U.S. Appl. No. 15/704,710, filed Sep. 14, 2017, 49 pages.

Cardinal, M. et al., "Intravascular Ultrasound Image Segmentation: A Fast-Marching Method," (2003), Springer, Berlin, Heidelberg 032548 XP055299068, vol. 2879, pp. 432-439.

Chalana, V. et al., "A Methodology for Evaluation of Boundary Detection Algorithms on Medical Images," IEEE Transactions on Medical Imaging, (Oct. 5, 1997) vol. 16, No. 5, pp. 643-645.

\* cited by examiner

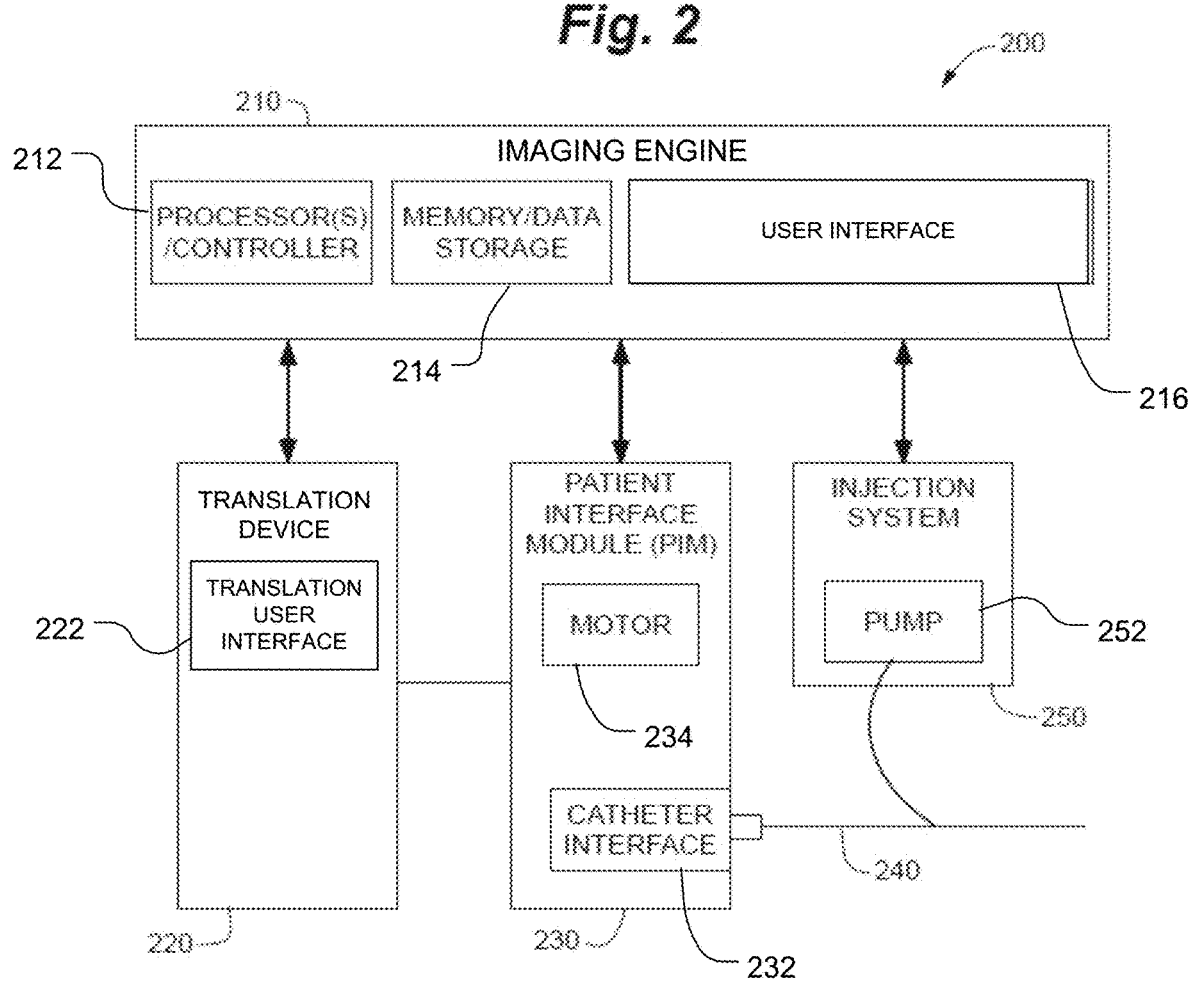

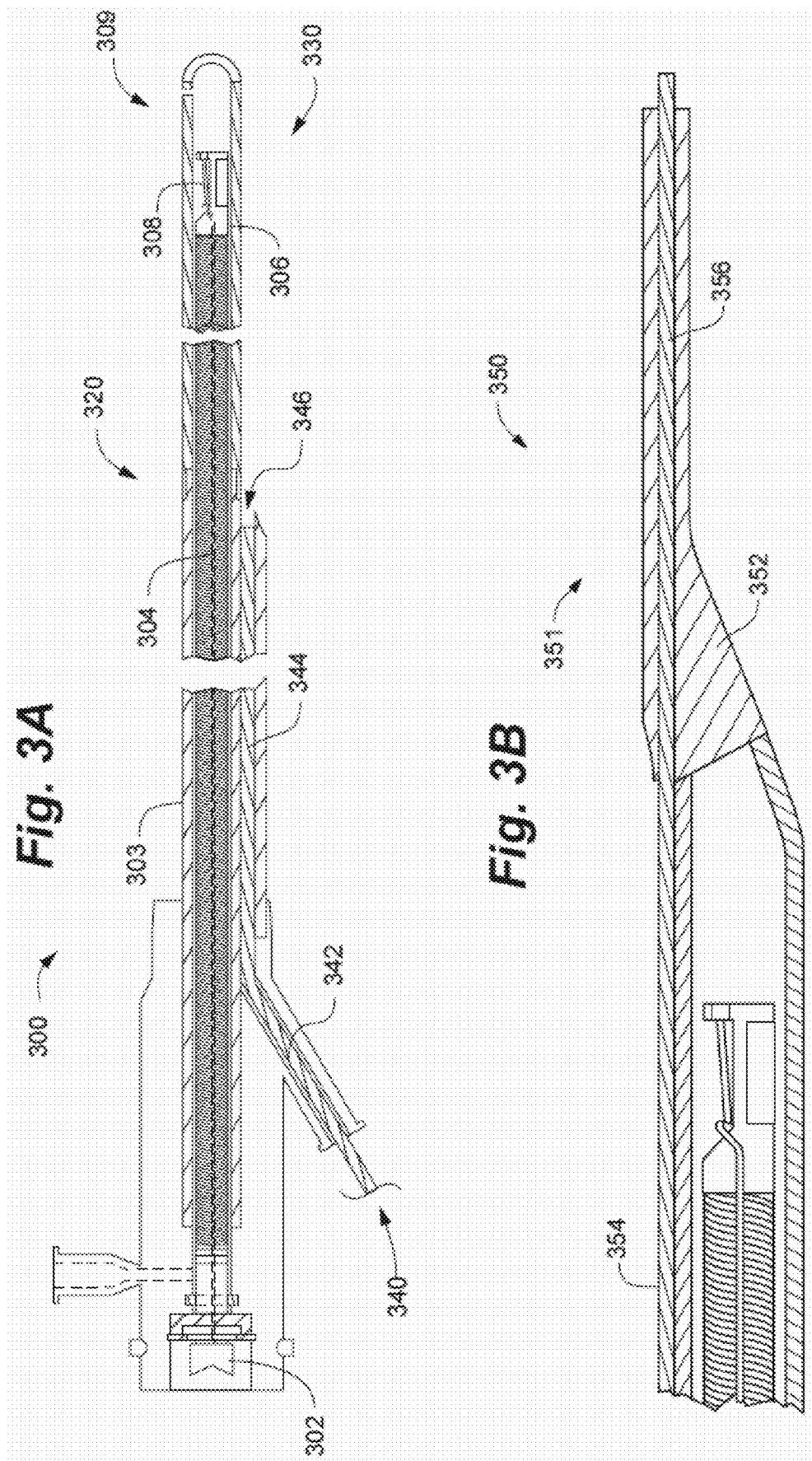

FIG. 4A
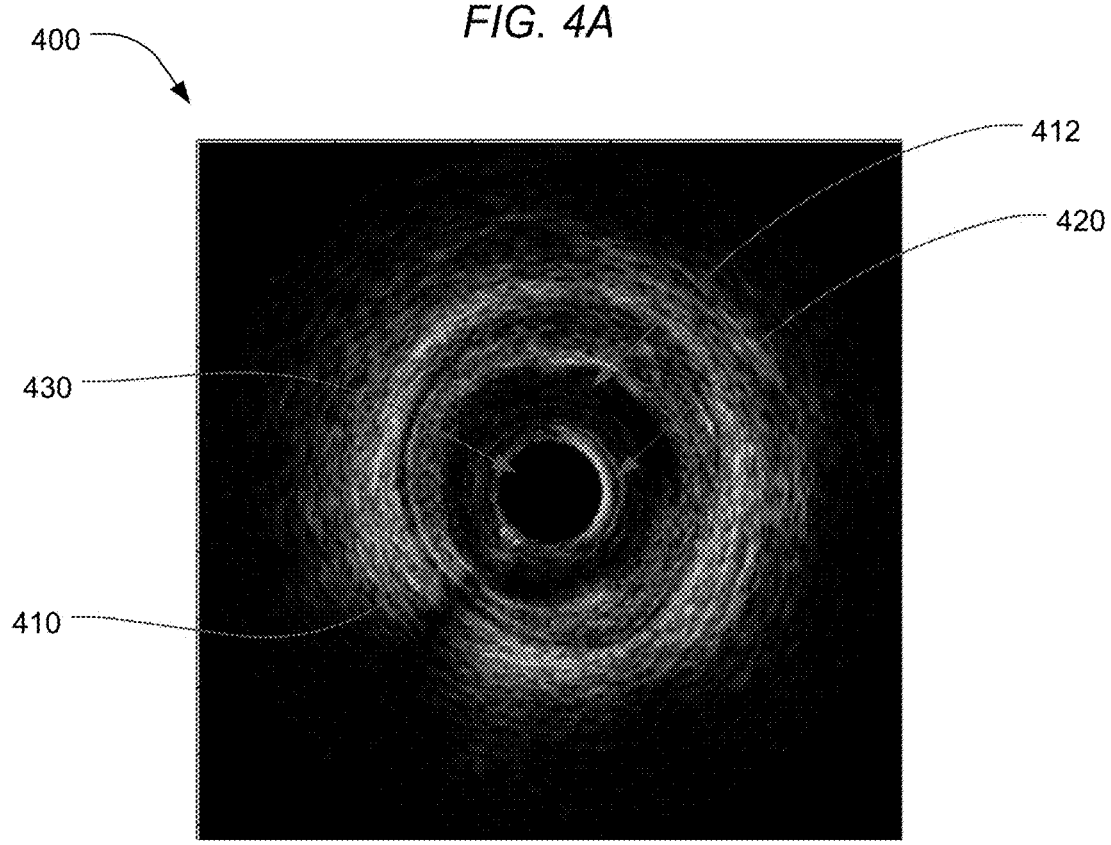
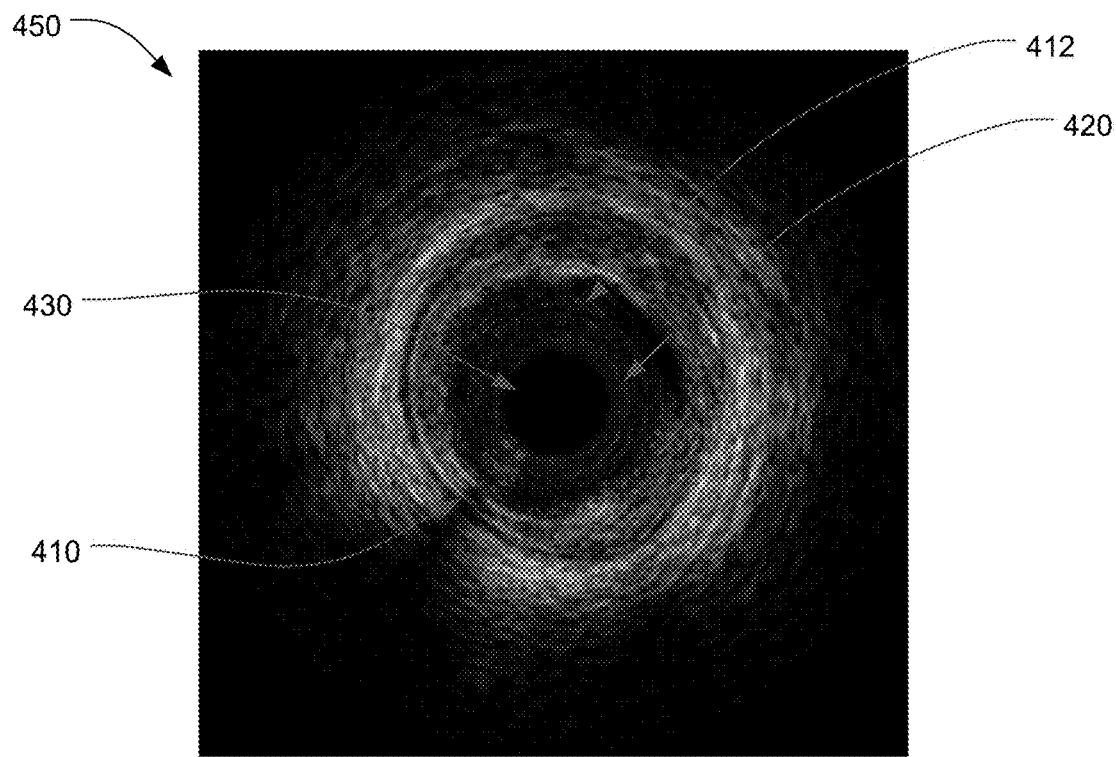
FIG. 4B

FIG. 5A
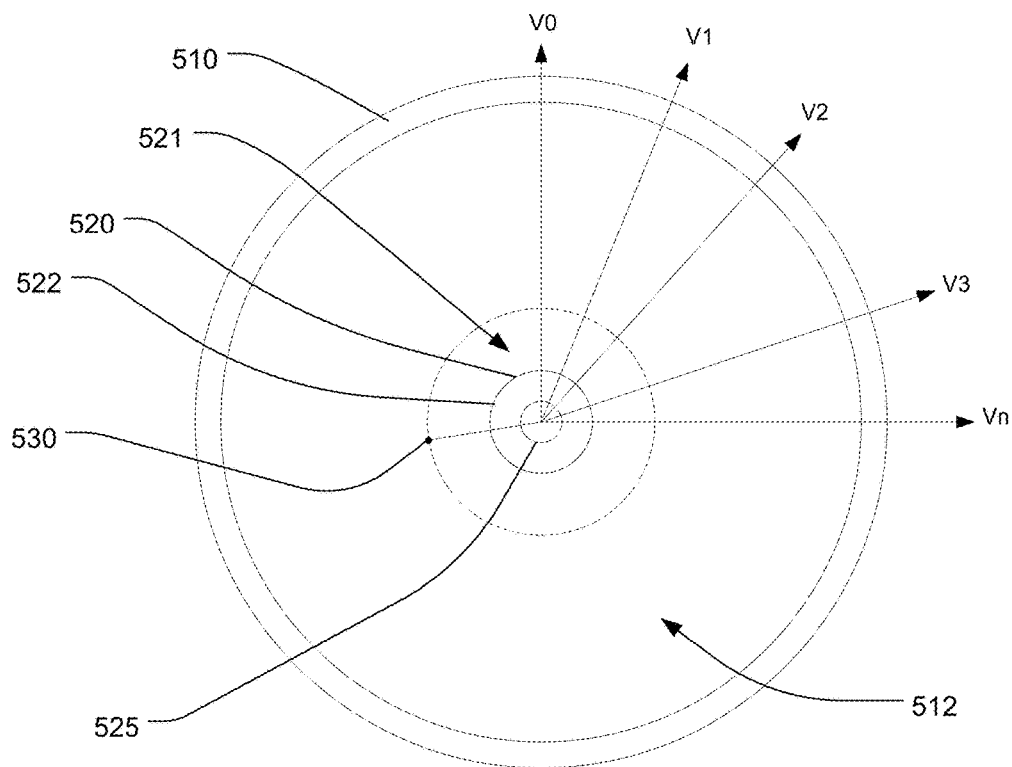
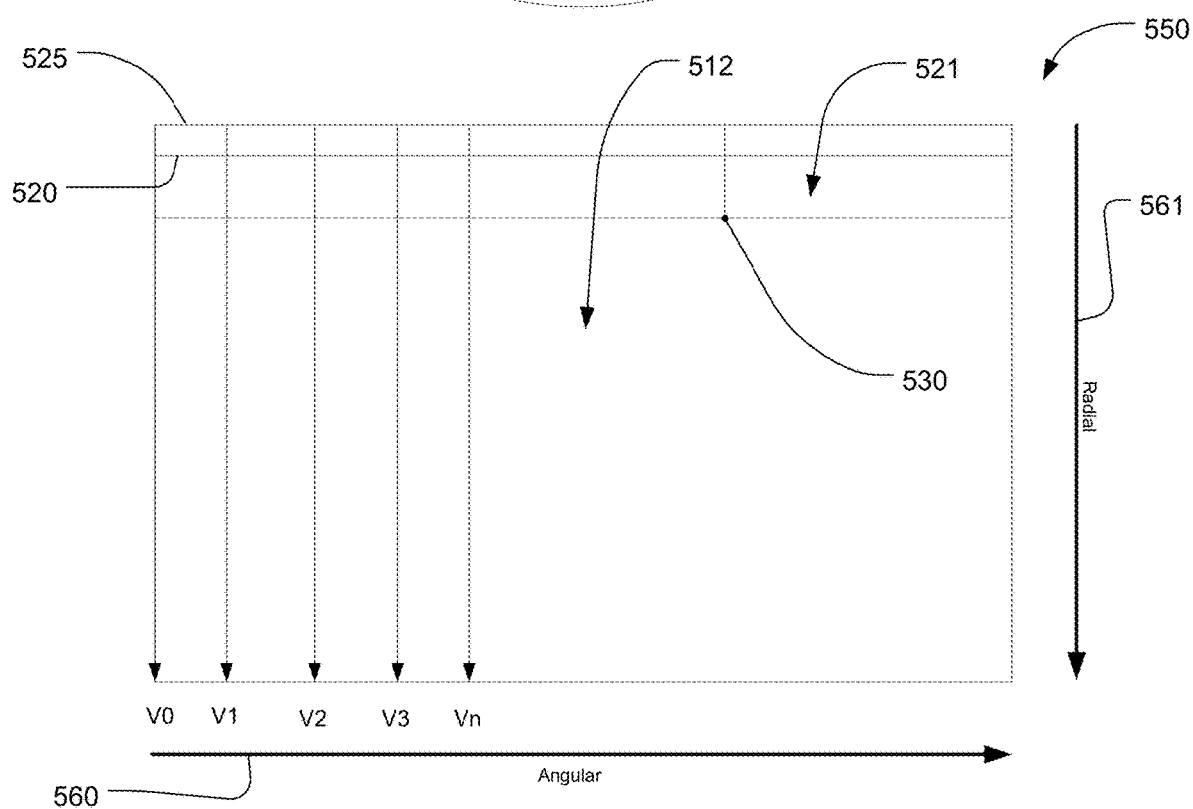
FIG. 5B

FIG. 7A
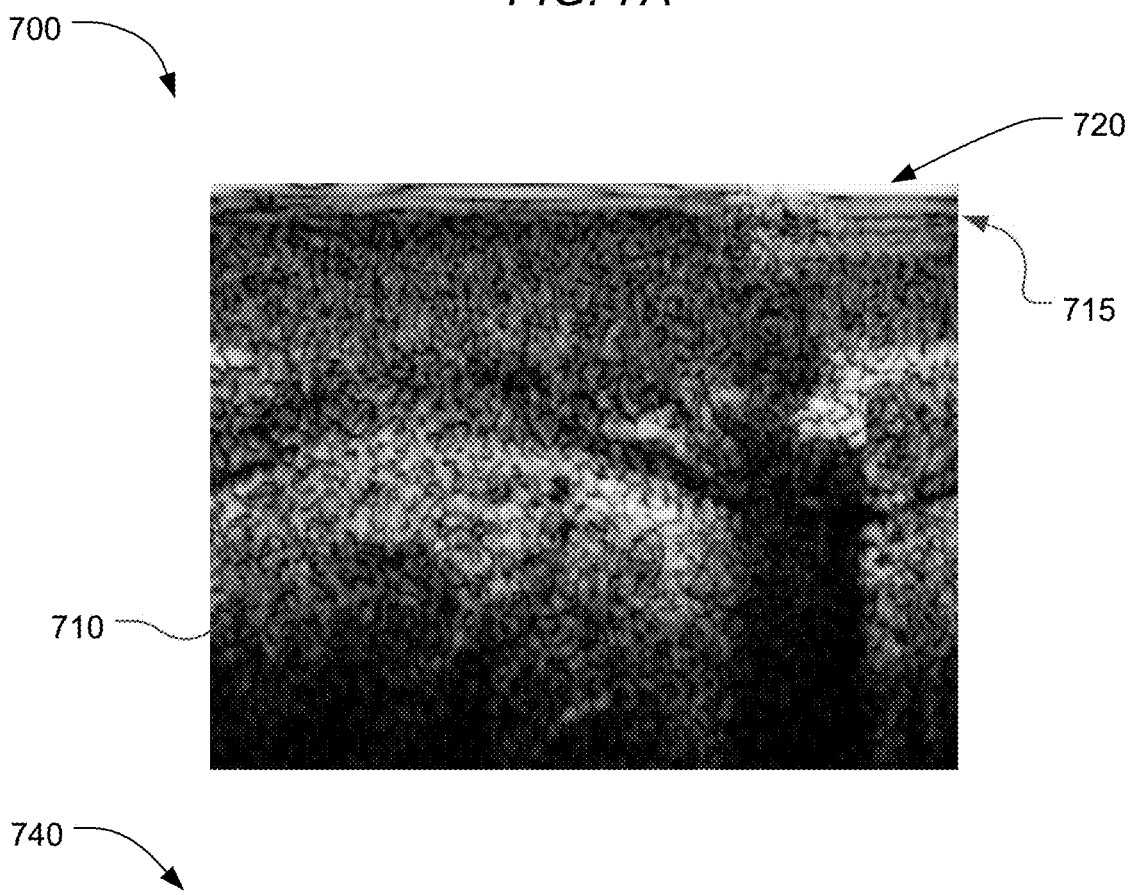
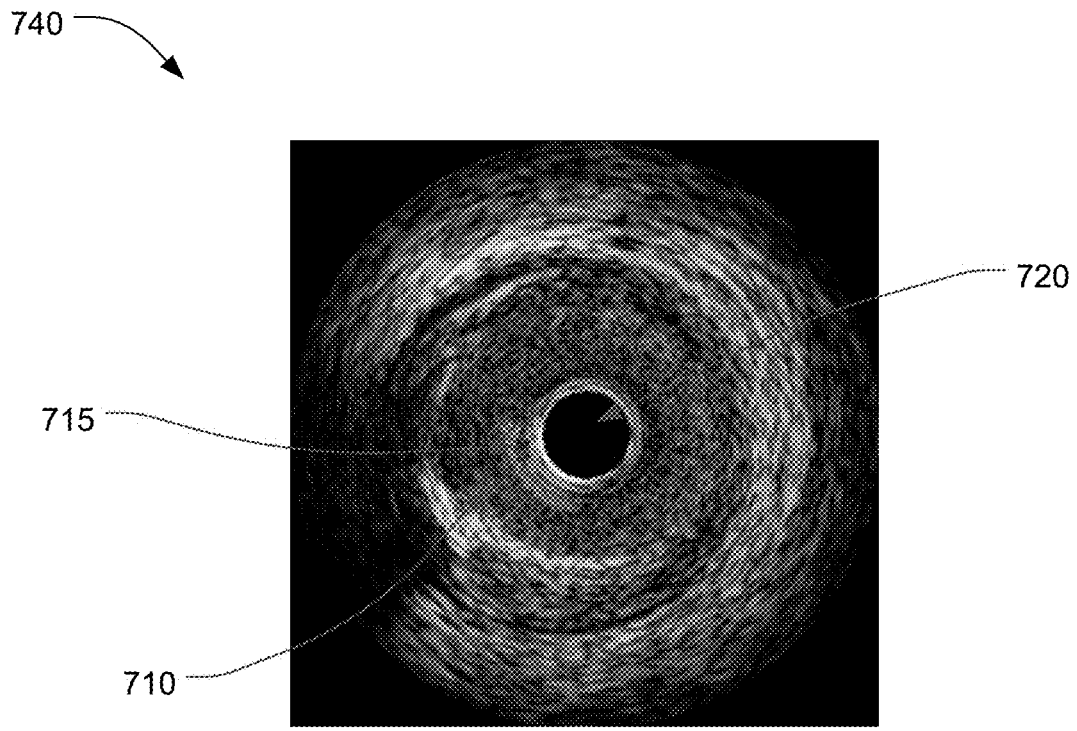
FIG. 7B

SYSTEMS AND METHODS TO REDUCE NEAR-FIELD ARTIFACTS

BACKGROUND

Medical imaging techniques generally can be used to collect data and generate in-vivo visualization of anatomical areas of interest. One such example is intravascular imaging, where vascular structures and lumens may be imaged. For instance, intravascular imaging may be used to produce one or more images of the coronary artery lumen, coronary artery wall morphology, and devices, such as stents, at or near the coronary artery wall. Images generated using medical imaging techniques can be useful for diagnostic purposes, such as identifying diagnostically significant characteristics of a vessel. However, generally information collected during medical imaging can include data that may not be relevant to the purpose for which the imaging is being performed, and, in some cases, may even obscure clinically useful data.

SUMMARY

Systems and methods are disclosed to reduce near-field artifacts from intravascular images. Catheter based intravascular imaging devices are susceptible to interference caused by a catheter body which can introduce near-field image artifacts in an intravascular image. Disclosed systems and methods are adapted to identify near-field image artifacts in imaging data and generate an enhanced intravascular image by reducing near-field image artifacts. One or more techniques can be used to reduce near-field image artifacts including spatial, circumferential, and/or radial filtering, as well as employing shader techniques.

BRIEF DESCRIPTION OF THE DRAWINGS

The following drawings are illustrative of particular embodiments of the invention and therefore do not limit the scope of the invention. The drawings are not necessarily to scale, unless so stated. The drawings are intended for use in conjunction with the explanations in the following detailed description. Embodiments of the invention will hereinafter be described in conjunction with the appended drawings, wherein like numerals denote like elements.

FIG. 2 is a block diagram illustrating a system configured to perform intravascular imaging.

FIG. 3A is a side cross-sectional view of an intravascular imaging device.

FIG. 3B is a side cross-sectional view of a distal section of a catheter assembly.

FIG. 4A illustrates a Cartesian image of a blood-cleared lumen including near-field artifacts.

FIG. 4B illustrates a Cartesian image of a blood-cleared lumen after near-field artifacts have been reduced.

FIG. 5A illustrates a catheter assembly disposed within a vessel.

FIG. 5B illustrates a polar format image of imaging data generated by a catheter assembly.

FIG. 7A illustrates a polar format image of a blood-filled lumen including near-field artifacts.

FIG. 7B illustrates a Cartesian image of a blood-filled lumen including near-field artifacts.

DETAILED DESCRIPTION

The following detailed description is exemplary in nature and is not intended to limit the scope, applicability, or configuration of the invention in any way. Rather, the following description provides some practical illustrations for implementing exemplary embodiments of the present invention. Examples of constructions, materials, and processes are provided for selected elements, and all other elements employ that which is known to those of ordinary skill in the field of the invention. Those skilled in the art will recognize that many of the noted examples have a variety of suitable alternatives.

Figure 1:
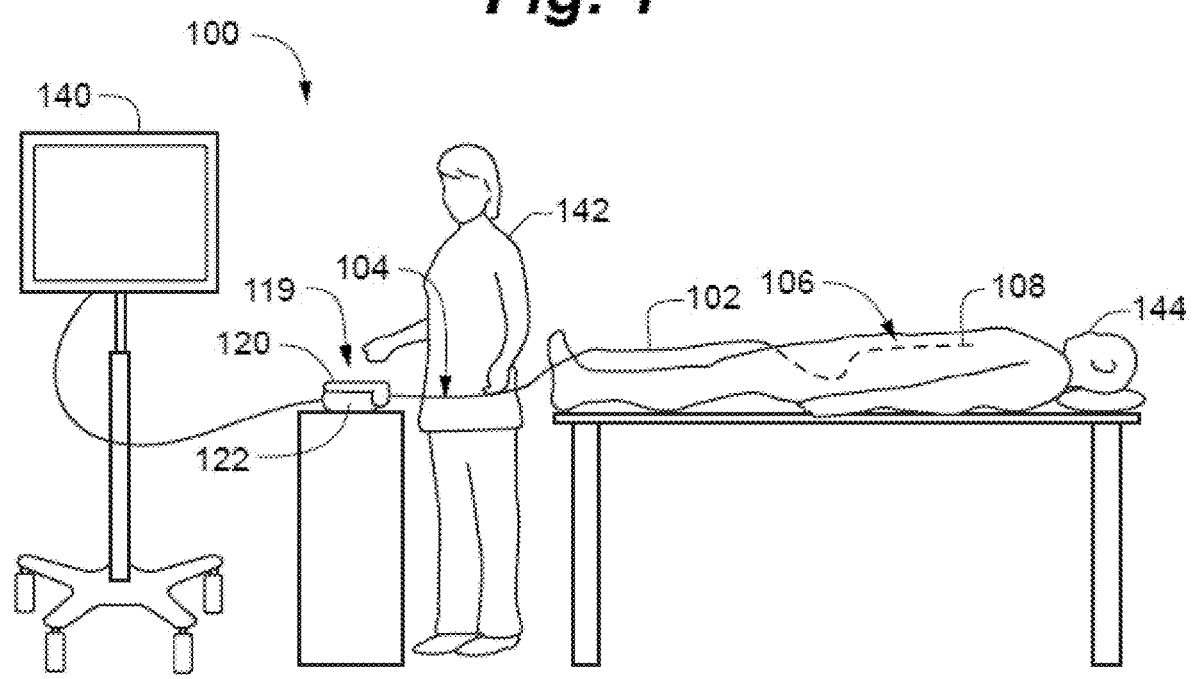
FIG. 1 is an illustrative example of a system configured to perform intravascular imaging.

FIG. 1 is an illustrative example of a system 100 that may be configured to perform intravascular imaging. System 100 can include catheter assembly 102, translation device 119, and imaging engine 140. The catheter assembly 102 may include a proximal end 104 and a distal end 106 configured to be inserted into a vessel of a patient 144. In one example, catheter assembly 102 may be inserted into the patient 144 via the femoral artery and guided to an area of interest within the patient 144. The broken lines in FIG. 1 represent portions of catheter assembly 102 within the patient 144.

Catheter assembly 102 can include an intravascular imaging device 108 adapted to generate imaging data. Intravascular imaging device 108 can be in communication with imaging engine 140. In some examples, intravascular imaging device 108 is an ultrasonic device adapted to emit and receive ultrasound energy and generate ultrasound data. In some examples, intravascular imaging device 108 is an optical coherence tomography (OCT) device adapted to emit and receive light and generate OCT data.

Translation device 119 can be configured to translate intravascular imaging device 108 of catheter assembly 102. The translation device 119 may comprise a linear translation system (LTS) 122. As is discussed elsewhere herein, LTS 122 may be mechanically engaged with catheter assembly 102 and configured to translate the catheter assembly 102 a controlled distance within the patient 144 during a translation operation, for example a pullback or push-forward operation. System 100 may comprise a patient interface module (PIM) 120 configured to interface the translation device 119 with the catheter assembly 102.

Imaging engine 140 can be in communication with intravascular imaging device 108 and translation device 119. According to some examples, the imaging engine 140 may comprise at least one programmable processor. In some examples, the imaging engine 140 may comprise a computing machine including one or more processors configured to receive commands from a system user 142 and/or display data acquired from catheter assembly 102 via a user interface. The computing machine may include computer peripherals (e.g., keyboard, mouse, electronic display) to receive inputs from the system user 142 and output system information and/or signals received from catheter assembly 102 (e.g., rendered images). In some examples, the user interface of the computing machine may be a touchscreen display configured to act as both an input device and an output device. In some examples, imaging engine 140 may include memory modules for storing instructions, or software, executable by the one or more processors.

The structure of imaging engine 140 can take a variety of forms. In some embodiments, the imaging engine can be made of an integrated machine that is configured to displace blood and to generate the screening and blood-displaced images. In some embodiments, the imaging engine can include separate injection and imaging apparatuses. In some such embodiments, the injection apparatus can be configured to displace blood, and the imaging apparatus can be configured to generate the screening and blood-displaced images. In some embodiments involving separate injection and imaging apparatuses, the two separate apparatuses can be configured to communicate and synchronize with one another. In some embodiments involving separate injection and imaging apparatuses, the injection apparatus can include a manual injection apparatus.

FIG. 2 is a block diagram illustrating system 200 adapted to perform intravascular imaging. System 200 can include PIM 230, translation device 220, injection system 250, catheter assembly 240, and imaging engine 210. System 200 can be configured to be used with an OCT and/or an IVUS based intravascular imaging device.

PIM 230 can provide an electromechanical interface between catheter assembly 240 and imaging engine 210. In some examples, PIM 230 may provide a catheter interface 232 to secure catheter assembly 240 to system 200. The PIM 230 may include a motor 234 configured to provide mechanical energy to rotate an intravascular imaging device of catheter assembly 240. According to some examples, PIM 230 may provide an electrical interface that transmits signals to the intravascular imaging device of catheter assembly 240 and receives return signals. In some examples, the intravascular imaging device may be electrically rotated via a phased array of ultrasound transducers.

Translation device 220 can be configured to provide longitudinal translation of catheter assembly 240. Translation device 220 may comprise a Linear Translation System (LTS). The translation device 220 may be configured to mate with PIM 230 and catheter assembly 240 to enable controlled pullback of an intravascular imaging device of catheter assembly 240.

According to some examples, translation device 220 may feature a translation user interface 222 which may comprise a translation display configured to display translation data associated with the translation of the intravascular imaging device to a user of system 200. In some examples, translation data may include linear distance traversed and/or translation speed. The translation user interface 222 may be configured to receive inputs from a user to control starting/stopping translation, setting translation speed, resetting linear distance traversed to zero, and/or switching to manual mode. In manual mode, a user may freely move the intravascular imaging device of the catheter assembly forward and backward (e.g., distally and proximally). In some examples, the translation device 220 may be configured to enable both pullback and push-forward of the intravascular imaging device at a controlled rate. In another example, the translation device 220 may be configured to oscillate, or cycle, the intravascular imaging device by alternately performing pullback and push-forward operations. In some examples, translation device 220 may include a position sensor configured to measure a distance of a translation operation.

Injection system 250 can be configured to deliver fluid into a vessel of a patient via catheter assembly 240. Injection system 250 may comprise an injector pump 252 configured to deliver one or more fluids (e.g., contrast, saline, therapeutic agent(s)) into the patient. In some examples, the injector pump 252 may be automated, in electrical communication with, and controlled by imaging engine 210. According to some examples, injector pump 252 may comprise a manual pump (e.g., syringe injection) configured to allow a user to manually deliver one or more fluids into the patient. As is discussed elsewhere herein, the injection system 250 may be in fluid communication with an intravascular blood displacement fluid port, which may be associated with catheter assembly 240, such that fluid from the injection system 250 is delivered into a patient's vasculature via the intravascular blood displacement fluid port. As can be appreciated, the injection system 250 may be configured to deliver any number of fluids and any quantity of fluid as appropriate for a specific application of system 200. In some examples, the quantity of blood displacement fluid may comprise a contrast media. In some examples, the quantity of blood displacement fluid may comprise saline.

FIG. 3A is a side cross-sectional view of a catheter assembly 300 that can be used in system 200 of FIG. 2. Referring again to FIG. 3A, a drive cable 304 of the catheter assembly 300 may be mechanically engaged and electrically connected to a PIM via a connector 302. Accordingly, the PIM may be used to rotate drive cable 304 within catheter sheath 303. Intravascular imaging device 309 may be coupled to drive cable 304 such that rotation of the drive cable 304 causes an imaging element 308 to rotate in a distal section 330 of the catheter assembly 300. The imaging element 308 may be configured to emit and receive wave-based energy and generate imaging data. The imaging data may then be communicated to an imaging engine where the imaging data may be rendered into an image. In examples where catheter assembly 300 is configured for use in an IVUS system, imaging element 308 may comprise an ultrasound transducer. In examples where catheter assembly 300 is configured for use in an OCT system, imaging element 308 may comprise an OCT imaging probe configured to emit and receive light. In some examples, catheter assembly 300 may include an imaging window 306 substantially transparent to the frequency of the wave-based energy emitted by imaging element 308.

As noted, in some examples, an injection system may deliver a quantity of fluid (e.g., a bolus of fluid) through an intravascular blood displacement fluid port into a vessel of a patient. In some such examples, catheter assembly 300 may include an injection cannula 342 in fluid communication with the injection system upstream of point 340. The injection cannula 342 can include an injection cannula lumen 344 and an intravascular blood displacement fluid port 346 for delivering the fluid into the vessel. The injection system may deliver small boluses of fluid (e.g., saline, contrast dye, therapeutic agent(s)) into the injection cannula lumen 344, out the intravascular blood displacement fluid port 346, and into the vessel. In other examples, the catheter assembly 300 need not include the injection cannula 342. Instead, the catheter assembly 300 can directly utilize the lumen in which the injection cannula 342 is disposed for conveying a quantity of fluid into the vessel at fluid port 346. The blood displacement fluid port 346 may be located in a proximal section 320 of the catheter assembly 300 upstream of imaging element 308 such that the injected bolus will travel along with the blood flow within the vessel (i.e., left to right with reference to FIG. 3A) towards the imaging element 308. The bolus may comprise fluid that is substantially transparent to the wavelength of the wave-based energy emitted by imaging element 308 and used as a flushing agent to clear the vessel of blood to allow for enhanced imaging of the vessel.

FIG. 3B is a side cross-sectional view of a distal section 350 of a catheter assembly. In some examples, distal section 350 may be used in lieu of distal section 330 included in catheter assembly 300 of FIG. 3A. Distal section 350 can be similar to distal section 330 of catheter assembly 300 except that distal section 350 may include a monorail guidewire system 351. The monorail guidewire system 351 may include a distal end 352 forming a guidewire lumen 356 configured to accept a guidewire 354 to guide the catheter assembly into a vascular system of a patient. It can be appreciated that different examples may be configured to accept different guidewires depending on the application of the catheter assembly.

Figure 3C:
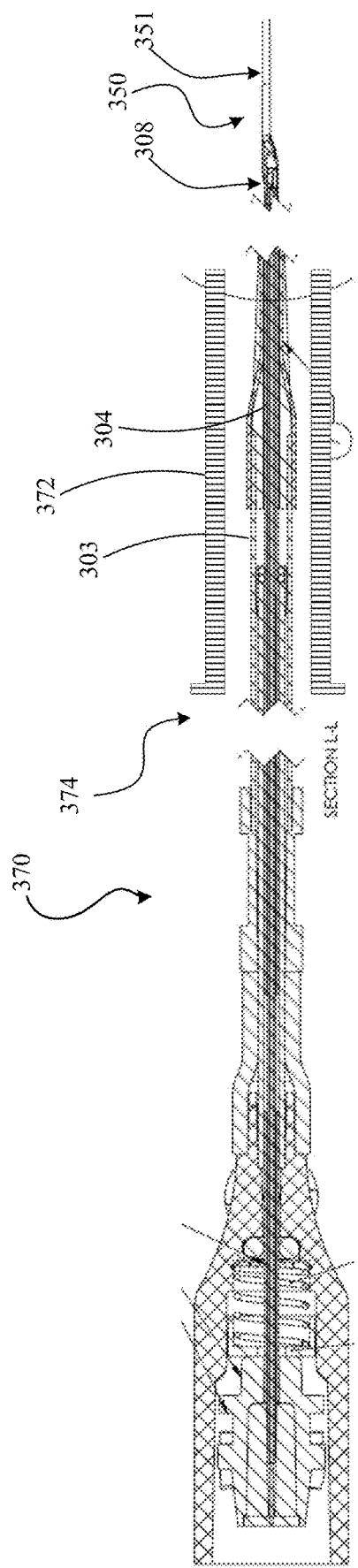
FIG. 3C is a side cross-sectional view of another embodiment of an intravascular imaging device.

FIG. 3C is a side cross-sectional view of another embodiment of a catheter assembly 370. In some examples, the catheter assembly 370 can be used in the system 200 of FIG. 2 or other similar systems. The catheter assembly 370 can include the catheter sheath 303 similar to that described for FIG. 3A, such that within the catheter sheath 303 there may be the drive cable 304 and imaging element 308. In the embodiment of the catheter assembly 370 shown in FIG. 3C, the catheter sheath 303 is disposed within a guide catheter 372, such that a space between the catheter sheath 303 and guide catheter 372 may be defined. In one application of the illustrated embodiment, the catheter sheath 303 can be delivered through the guide catheter 372, such as over the guidewire system 351. In some such embodiments, the catheter assembly 370 can have the distal section 350 similar to that shown and described in FIG. 3B.

The injection system can be used to deliver a quantity of fluid (e.g., a bolus of fluid) into a vessel of a patient using the space defined between the catheter sheath 303 and guide catheter 372. In such embodiments, the space defined between the catheter sheath 303 and guide catheter 372 can serve the function of the injection cannula as described for FIG. 3A without needing to have the injection cannula itself. In one example, the guide catheter 372 can define an inlet in fluid communication with the injection system. As such, the guide catheter can receive small boluses of fluid (e.g., saline, contrast dye, therapeutic agent) at the defined inlet and convey these boluses within the space defined between the catheter sheath 303 and guide catheter 372 to an intravascular blood displacement fluid port, which may be located in a proximal section 374 and upstream of the imaging element 308.

Referring back to FIG. 2, imaging engine 210 of system 200 can be adapted to perform one or more functions. In some examples, imaging engine 210 can be adapted to generate intravascular images, display intravascular images and other information, control components of system 200, analyze imaging data (e.g., area measurements, linear measurements, and annotations), perform hemodynamic calculations, and so on. As will be discussed further below, imaging engine 210 can also be adapted to reduce near-field artifacts from imaging data. Imaging engine 210 can include processor 212, computer storage article 214, and user interface 216.

Computer storage article 214 can be adapted to store instructions executable by processor 212 (e.g., software). In some examples, computer storage article 214 can include one or more non-transitory computer readable storage media which may include volatile and/or non-volatile memory including, e.g., random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media as appropriate for a specific purpose. In some examples, instructions can be embedded or encoded in computer storage article 214 which can cause processor 212 to perform a method, e.g., when the instructions are executed. For example, computer storage article 214 can store program modules adapted to execute on processor 212. As will be discussed further herein, in some examples the stored program modules can include a receiving module, a detection module, and an image processing module.

System 200 can be adapted to reduce near-field artifacts in an intravascular image. In some examples, near-field artifacts can be caused by interference associated with a catheter. For example, with reference to FIG. 3A, wave-based energy emitted and received by imaging element 308 must pass through catheter sheath 303, which can cause near-field artifacts in imaging data generated by imaging element 308. It has been found that near-field artifacts can also be present in examples where a catheter includes imaging window 306, even though the imaging window 306 is adapted to be substantially transparent to the frequency of the wave-based energy emitted by imaging element 308.

FIG. 4A illustrates a Cartesian image 400 of vessel 410 defining a blood-cleared lumen 412, where the lumen includes near-field artifact 420. As noted above, disclosed systems and methods can be adapted to reduce near-field artifacts. For example, FIG. 4B illustrates Cartesian image 450 of vessel 410 after near-field artifact 420 has been reduced. It can be appreciated that there are numerous benefits related to intravascular imaging devices adapted to reduce near-field artifacts. For example, such devices can have substantial diagnostic benefits as they will increase the accuracy and image quality of an intravascular image.

FIG. 5A is a cross-section of catheter assembly 520 disposed within vessel 510 defining a lumen 512. Catheter assembly 520 can include intravascular imaging device 525 disposed within catheter body 522. Intravascular imaging device 525 can be adapted to image vessel 510 by continuously rotating an imaging element which generates imaging data by emitting and receiving wave-based energy. In this example, imaging vectors V0-Vn are representative of imaging data associated with sequentially emitting and receiving wave-based energy from an imaging element being rotated clockwise. An imaging engine can be adapted to combine the imaging vectors to generate an image of vessel 510.

As noted above, near-field artifacts can be caused when a catheter body interferes with the emission and reception of wave-based energy. More specifically, catheter body 522 can interfere with the emission and reception of wave-based energy from imaging device 525 to cause near-field artifacts in artifact area 521. In some examples, artifact area 521 can be a subset of the imaging data that includes, or is likely to include, a near-field artifact. The size of artifact area 521 can correspond with an area within artifact distance 530 of imaging device 525. As will be discussed further below, artifact distance 530, and consequently the size of artifact area 521, can be predetermined or dynamically calculated to facilitate reduction of near-field artifacts.

FIG. 5B illustrates a polar format image 550 of imaging data generated by catheter assembly 520 of FIG. 5A. In some examples, an imaging engine can be adapted to generate polar format image 550 by combining imaging vectors generated by imaging device 525 of FIG. 5A. Imaging vectors can be sequentially combined, for example as illustrated by the sequential transposition of imaging vectors V0-Vn onto polar format image 550. In such examples, polar format image 550 has an angular gradient from left to right as illustrated by axis 560. In some examples, polar format image 550 corresponds to one complete revolution of the imaging element. The one complete revolution of the imaging element may occur, in some applications, at a constant spatial (e.g., longitudinal) location within the vessel. Polar format image 550 can also have a radial distance gradient from top to bottom as illustrated by axis 561.

As in FIG. 5A, artifact area 521 corresponds to an area within artifact distance 530 of imaging device 525 wherein near-field artifacts are can be present in the imaging data. As will be discussed further below, a radial filter can be used to reduce near-field artifacts within artifact area 521 by identifying and reducing near-field artifacts along the radial distance gradient, illustrated for example by axis 561. Similarly, a spatial filter (e.g., spatial in terms of image features) can be used to reduce near-field artifacts within artifact area 521 by identifying and reducing near-field artifacts along the angular gradient, for example as illustrated by axis 560. In some examples, an imaging engine can be adapted to generate a Cartesian image from a polar format image or directly from generated imaging data. In such examples, the imaging engine can be adapted to identify and reduce near-field artifacts within an artifact area of the Cartesian image using a circumferential filter.

Figure 6A:
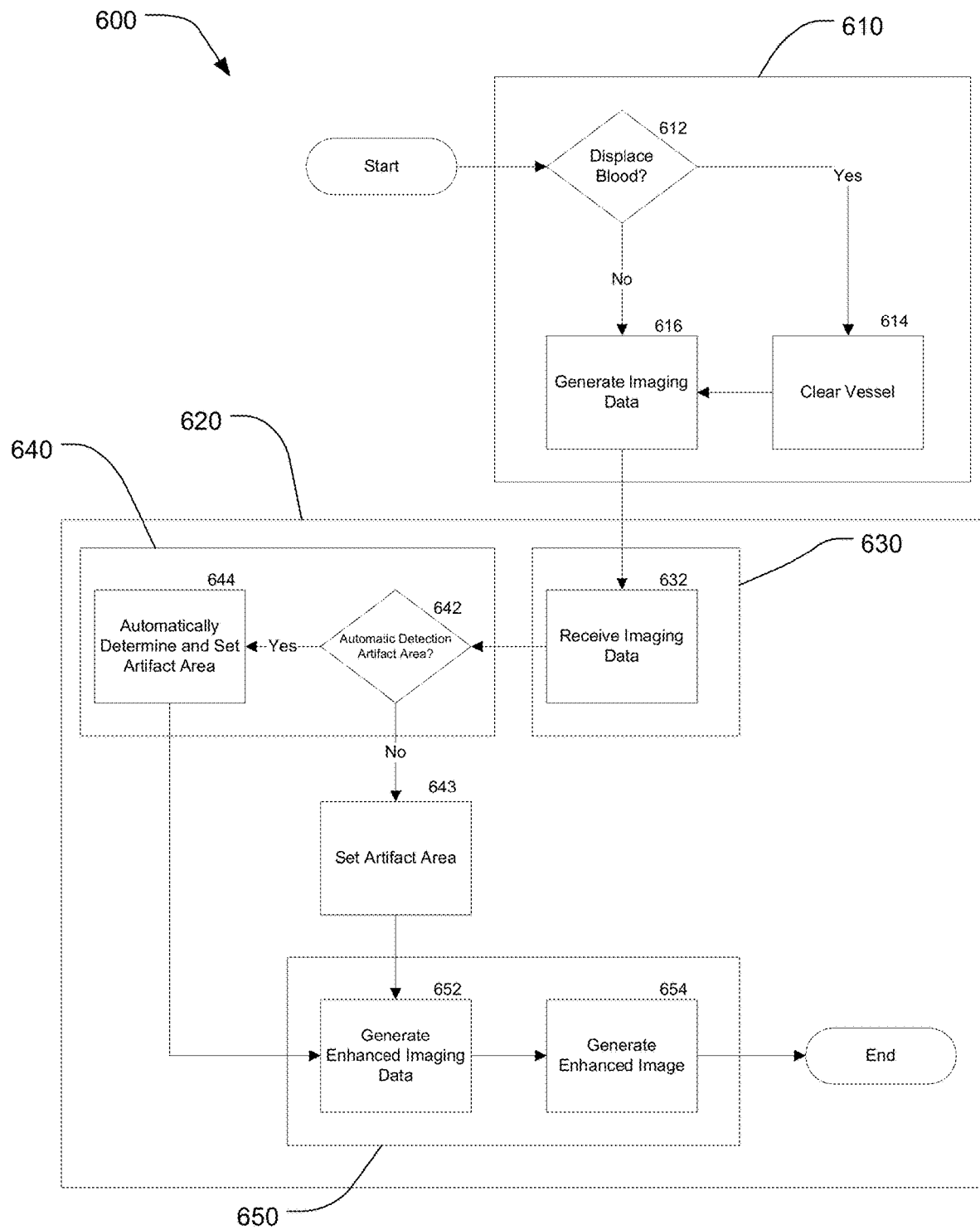
FIG. 6A is a flow diagram illustrating a method for reducing near-field artifacts.

FIG. 6A is a flow diagram illustrating a method 600 for reducing near-field artifacts. In some examples, method 600 can be performed by catheter assembly 610 and imaging engine 620. Imaging engine 620 can include receiving module 630, detection module 640, and image processing module 650. Similar to examples disclosed above, catheter assembly 610 can be in communication with imaging engine 620.

In some examples, catheter assembly 610 can be adapted to provide the option to displace blood 612 from a vessel before imaging the vessel. Where catheter assembly is adapted to displace blood, catheter assembly 610 can be adapted to clear 614 the vessel before generating 616 image data. Clearing 614 the vessel of blood can reduce interference for ultrasound based imaging elements or provide line of sight for OCT based imaging element.

Receiving module 630 of imaging engine 620 can be adapted to receive 632 imaging data. In some examples, receiving module 630 is adapted to receive 632 imaging data from an intravascular imaging device of catheter assembly 610. Receiving module 630 can also receive imaging parameters/settings from catheter assembly 610. In such examples, imaging parameters/settings can be used to facilitate reduction of near-field artifacts as the manifestation of near-field artifacts in imaging data can vary depending on the imaging parameters/settings. Imaging parameters/settings that can be taken into account when reducing near-field artifacts can include, but is not limited to, a type of catheter body (e.g., construction/material), whether vessel is cleared of blood, and imaging frequency.

Detection module 640 of imaging engine 620 can be adapted to provide the option to automatically determine 642 an artifact area and automatically set 644 an artifact area. In some examples, detection module 640 can be adapted to automatically set 644 the artifact area based on imaging parameters passed to imaging engine 620 from catheter assembly 610. In some examples, detection module 640 can be adapted to automatically set 644 the artifact area by analyzing the imaging data to identify a subset of imaging data wherein near-field artifacts are present and setting the artifact area to include the subset of imaging data.

Automatically setting 644 the artifact area can vary depending on whether the application involves a blood-filled lumen or a blood-cleared lumen. In examples associated with blood-filled lumens, detection module 640 can be adapted to detect artifacts having arcs greater than 45 degrees in a Cartesian image. In similar examples, detection module 640 can be adapted to detect artifacts in a blood-filled lumen having an angular spatial frequency less than 0.8 radians. Similarly, detection module 640 can be adapted detect artifacts having a radial spatial frequency between 6/mm and 8/mm in a polar format image. In some examples, detection module 640 can be adapted to detect artifacts that repeat every 12 to 18 points in a radial direction of a polar format image. In examples associated with blood-cleared lumens, detection module 640 can be adapted to detect artifacts having arcs greater than 10 degrees in a Cartesian image. In similar examples, detection module 640 can be adapted to detect artifacts in a blood-cleared lumen having an angular spatial frequency less than 0.2 radians.

The feature of providing the option to automatically determine 642 and setting 644 an artifact area provides the advantage of minimizing the processing power and time required to reduce near-field artifacts within the artifact area. More specifically, steps 642 and 644 helps to ensure that resources are used to enhance only imaging data likely to include near-field artifacts. This benefit is particularly advantageous where catheter assembly 610 is adapted to provide a live view of a vessel where increased processing time can increase latency of the image.

Another advantage provided by steps 642 and 644 is that imaging engine 620 can be configurable to work together with a plurality of catheter assemblies. It has been found that the size and/or nature of near-field artifacts can vary based on the method of intravascular imaging. For example, it has been discovered that near-field artifacts are larger when imaging a blood-cleared lumen as compared to a blood-filled lumen. Similarly, the manifestation of near-field artifacts in imaging data can be affected by size, shape, and thickness of a catheter body, material from which a catheter body and/or imaging window is made, imaging frequency of the imaging element, a position of the transducer, and/or wall thickness. Accordingly, imaging engine can be used together with a variety of catheter assemblies where imaging engine 620 is adapted to account for these various factors when reducing near-field imaging artifacts.

In examples where detection module 640 does not automatically determine the artifact area, the artifact area can be set 643 manually or predefined by a user. In one application, an imaging device can have a field of view with a radius of approximately 4 mm, measured from a center of the imaging device. Thus, the imaging device can collect image data relating to items within this 4 mm radius (or 8 mm diameter) at the particular longitudinal location within the vessel. A distance from the center of imaging device to the catheter body can be approximately 0.5 mm along the field of view radius, such that the imaging device's field of view outside the catheter is approximately 3.5 mm. In one example, an artifact distance of 1.5 mm can be manually set or predefined. In other examples, an artifact distance of 1 mm can be manually set or predefined. In some examples, an artifact distance between 0.5 and 1 mm can be manually set or predefined. In some examples, an artifact distance between 0.25 and 1.5 mm can be manually set or predefined. In some examples, an artifact area can correspond with a number of rows of imaging data adjacent to an imaging element, for example as depicted in a polar format image. In some examples, the artifact area corresponds with the first 76 rows of the imaging data adjacent to the imaging element. In other examples, the filter area corresponds with the first 100 rows of the imaging data adjacent to the imaging element. The ranges disclosed above can be associated with near-field artifacts in intravascular ultrasound imaging. It can be appreciated that other artifact distances are contemplated and can vary as necessary for a particular application/use and are within the spirit of this disclosure. For instance, a manually set or predefined artifact area can be a function of the particular catheter assembly being used (e.g., dimensions of the catheter assembly, such as a distance from a center of imaging device to the catheter body).

Image processing module 650 of imaging engine 620 can be adapted to generate 652 enhanced imaging data. In some examples, enhanced imaging data can be generated 652 by reducing a near field artifact from the imaging data using a variety of techniques. In some examples, image processing module can be adapted to generate 654 an enhanced image from the enhanced imaging data and display the enhanced image on a display. The enhanced image generated 654 can be in any suitable format, for example Cartesian format or polar format.

Figure 6B:
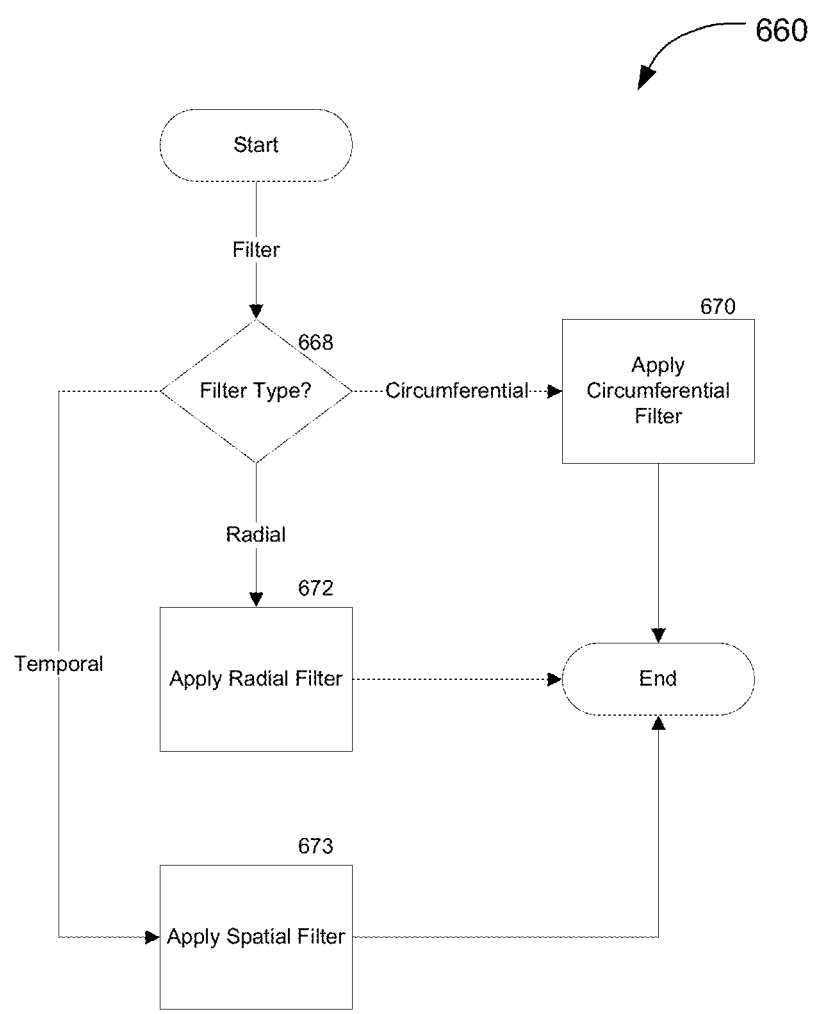
FIG. 6B is a flow diagram illustrating a method for generating enhanced imaging data.

FIG. 6B is a flow diagram illustrating a method 660 for generating enhanced imaging data. Method 660 can be performed by an image processing module of an imaging engine, for example in step 652 of method 600. For example, an image processing module can be adapted to reduce near-field artifacts from imaging data by applying a filter to remove or reduce the artifact data from the generated data set. In other examples, various other techniques suitable for reducing the near-field artifact within an artifact area can be incorporated into the method 660 in conjunction with, or as an alternative to, application of one or more filters.

Where a filter is used to reduce near-field artifacts from imaging data, step 668 determines an appropriate filter type. An appropriate filter can include, as one example, application of a sufficient blur to accomplish a low-pass filter. In this example, method 660 is adapted to apply 670 a circumferential filter, apply 672 a radial filter, and/or apply 673 a spatial filter. In some examples, the filters can be iteratively applied. As noted above, in some examples radial filters and spatial filters can be used to reduce near-field artifacts in polar format images, and circumferential filters can be used to reduce near-field artifacts in Cartesian images.

An image processing module can be adapted to apply 670 a circumferential filter. In some examples, a circumferential filter can be adapted to reduce near-field artifacts by filtering an arc associated with the near-field artifact from the imaging data. The circumferential filter can be adapted to filter arcs greater than 45 degrees for imaging data associated with blood-filled lumens, and greater than 10 degrees in blood-cleared lumens. Similarly, the circumferential filter can be adapted to filter artifacts have an angular spatial frequency less than 0.8 radians for imaging data associated with blood-filled lumens, and less than 0.2 radians in blood-cleared lumens.

An image processing module can be adapted to apply 672 a radial filter. In some examples, a radial filter can be adapted to filter artifacts having a radial spatial frequency between 6/mm and 8/mm in a polar format image. Similarly, a radial filter can be adapted to filter artifacts that repeat every 12 to 18 points in a radial direction of a polar format image.

In some examples, an image processing module can be adapted to apply 673 a spatial filter. For instance, a high-pass spatial filtered image can be calculated by first utilizing a low-pass spatial filter (e.g., low-pass Gaussian filter) to obtain low-pass filtered image data. The low-pass filtered image data can then be subtracted from the original image data (e.g., generated by the imaging device) to obtain high-pass filtered image data. In various embodiments, utilizing a spatial high-pass filter can be beneficial because the image data corresponding to near-field artifacts may have relatively more low frequency content as compared to other items of the imaged vessel (e.g., blood, tissue).

In some examples of the method 660, an image processing module can be adapted to apply a multi-pass per data point of the appropriate one or more filters selected at step 668 (e.g., a shader technique) to reduce one or more near-field artifacts. A shader technique can involve a multi-pass per data point application of one or more filters in a parallel (e.g., vectorized) operation. Shader techniques may be amenable to operations performed via a graphics processing unit (GPU) included in the image processing module, as opposed to non-shader techniques (e.g., a single pass per data point) performed in non-parallel manner on a central processing unit (CPU). In one example, applying a shader technique can include applying a first filter to image data (e.g., a data point). The first filter can be, for instance, a radial, spatial, or circumferential filter. Then, a second filter can be applied to the image data upon which the first filter was applied. This process can be repeated for an appropriate number of passes (e.g., a third filter can be applied to the image data upon which the second filter was applied) to accomplish multi-pass filtering of the same image data. Thus, the method 660 can include multiple uses of a filter on a single data point.

FIG. 7A illustrates a polar format image 700 of blood-filled lumen 710 including catheter assembly 720. The polar format image 700 includes near-field artifact 715. In this example, near-field artifact 715 can be reduced by an imaging engine using a temporal filter, radial filter, and/or shader technique.

FIG. 7B illustrates a Cartesian image 740 of blood-filled lumen 710 including near-field artifact 715 of FIG. 7A. In this example, near-field artifact 715 can be reduced by an imaging engine using a circumferential filter and/or shader technique.

Figure 7C:
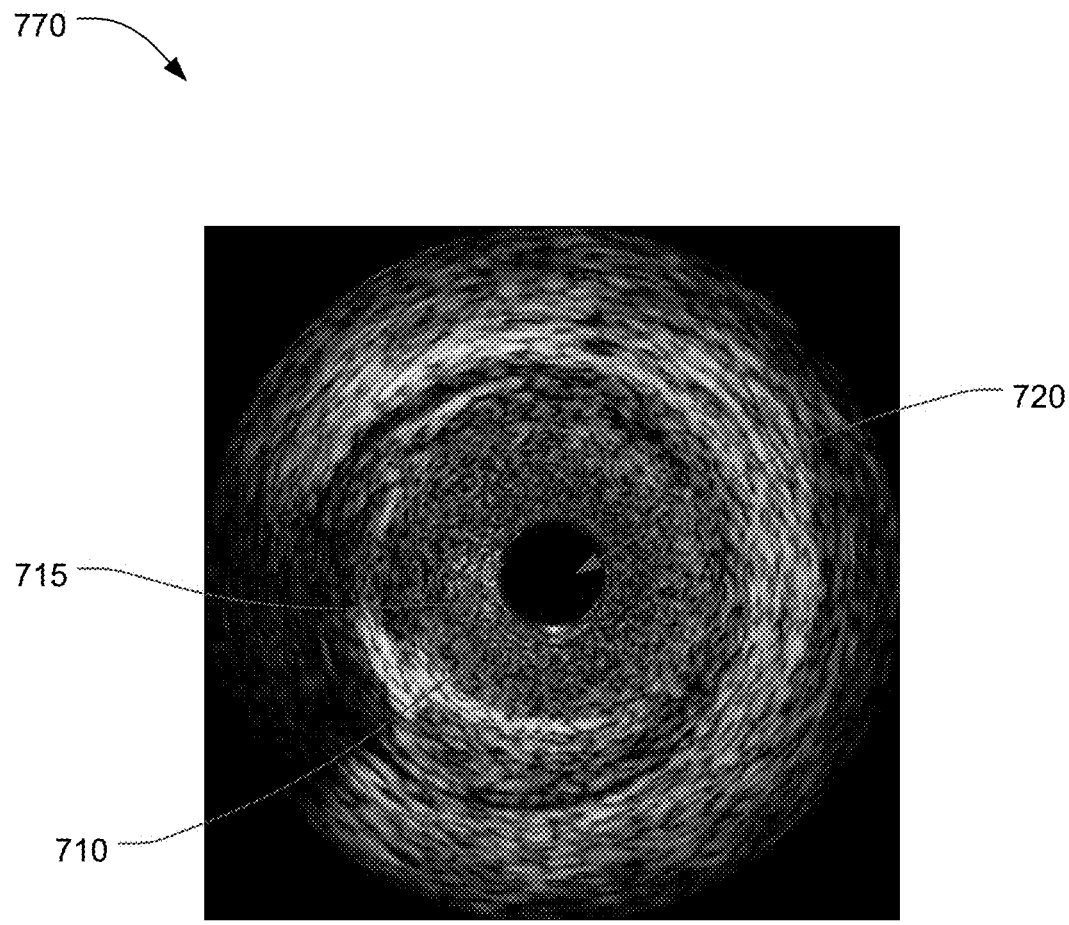
FIG. 7C illustrates an enhanced Cartesian image of a blood-filled lumen with near-field artifacts reduced.

FIG. 7C illustrates an enhanced Cartesian image 770 of blood-filled lumen 710 with near-field artifact 715 reduced. In one example, enhanced Cartesian image 770 is generated by reducing near-field artifacts in polar format image 700 then converting the enhanced polar format image into a Cartesian image. In another example, polar format image can be converted to Cartesian image 740, and then near-field artifacts can be reduced in the converted Cartesian image to generate enhanced Cartesian image 770.

Depending on the application in which imaging data is generated, it may be useful to apply one or more of the described operations across multiple frames of imaging data to reduce near-field artifacts. As detailed previously, an imaging device can be configured to generate and receive wave-based energy by rotating at a specific longitudinal location within a vessel. A frame of imaging data can include imaging data generated at the specific longitudinal location within the vessel (e.g., based on a 360 degree rotation of the imaging device at that location). The imaging device can translate longitudinally within the vessel, to a different longitudinal location within the vessel, and generate a second frame of imaging data representative of the new longitudinal location within the vessel. As will be appreciated, a period of time elapses between the times at which the first and second frames are generated. Furthermore, the greater the longitudinal distance within the vessel between any two frames, the greater the period of time will be between these frames.

In utilizing multiple frames of imaging data to reduce near-field artifacts, a first frame of imaging data is designated as a key frame (e.g., a first frame). One or more other frames can be designated as reference frames (e.g., second and third frames). In one instance, the key frame and one or more reference frames may be neighboring frames that are adjacent one another along the longitudinal direction of the vessel. For example, the key frame can have first and second reference frames as the respective forward and backward immediately adjacent frames. In other instances, the key frame and one or more reference frames can be spaced apart by any number of other frames. In some examples, the key frame can be spaced apart from one or more reference frames by 2, 3, 4, 5, 10, 20, 25, 50, or 100 frames as examples. In some cases, the key frame can be spaced apart from one or more reference frames by between 2 and 50 frames, 2 and 25 frames, 2 and 10 frames, or 2 and 5 frames. The further spaced apart the key frame is from the one or more reference frames (e.g., the greater the number of frames between the key frame and the one or more reference frames), the greater the period of time will be between generation of the imaging data of the key and reference frame(s).

In one exemplary embodiment, a key frame and two reference frames can be selected, where multiple other frames are generated at longitudinal locations between the longitudinal location corresponding to each of the key and reference frames (e.g., the key and reference frames are not adjacent frames). As such, a period of time may pass between the imaging data generated for the selected key and reference frames (e.g. a greater period of time as compared to the selected key and reference frames being adjacent frames). Selecting key and reference frames that are spaced apart in time can allow the selected key and reference frames to capture useful vessel information. For instance, key and reference frames that are far away in time can include image data representing tissue movement ascertainable when the key and reference frames are compared. Such information can be used in generating an enhanced image data.

A filter can be applied to each of the selected key and two reference frames. In particular, the filter may be applied to the artifact area of each of the selected key and two reference frames. As described previously, the artifact area of each frame may be determined automatically or set manually. In one example, the filter applied to the artifact area of each of the selected key and two reference frames can, for instance, be a low-pass filter. Applying the low-pass filter to the artifact area of each of the selected key and two reference frames can include applying circumferential, radial, and/or spatial filters, and in some case can include, additionally or alternatively, the use of a shader technique.

For instance, in one application a radial filter is applied to the artifact area of each of the selected key and two reference frames. In addition, a circumferential filter is applied to the artifact area of each of the selected key and two reference frames. In such an example, an additional filter can be applied to the artifact area of each of the selected key and two reference frames on a per pixel basis across the selected frames. The per pixel filter can be taken, for instance, using a minimum pixel value. Once the described filtering of the present example has been applied, the resulting filtered key and two filtered reference frames can each be subtracted from the originally generated image data corresponding to the selected key and two reference frames.

Filtering across multiple frames can allow for determination of movement of low frequency data. If movement of low frequency data is detected, then this can indicate that the identified portion of image data represents, for example, tissue that may not be desirable to filter out of an enhanced image in many applications. Near-field artifacts generally will not substantially move across multiple frames, and ascertaining such information in the imaging data can allow near-field artifacts to be filtered out when generating an enhanced image. Thus, in many applications low frequency image data that does not move between frames indicates that such data represents an artifact that can be filtered out when generating an enhanced image.

Various examples of the invention have been described. Although the present invention has been described in considerable detail with reference to certain disclosed embodiments, the embodiments are presented for purposes of illustration and not limitation. Other embodiments incorporating the invention are possible. One skilled in the art will appreciate that various changes, adaptations, and modifications may be made without departing from the spirit of the invention and the scope of the appended claims.

What is claimed is:

1. A system comprising:
   (a) a catheter assembly including a catheter body and an intravascular imaging device located within the catheter body and being adapted to generate imaging data, the intravascular imaging device including an imaging element; and
   (b) an imaging engine in communication with the intravascular imaging device, the imaging engine adapted to
      (i) receive the imaging data from the intravascular imaging device, wherein the imaging data received from the intravascular imaging device comprises at least a first frame of imaging data and a second frame of imaging data, wherein the first frame of imaging data and the second frame of imaging data are not adjacent frames, wherein the first frame comprises a key frame, and wherein the second frame comprises a reference frame,
      (ii) detect a near-field artifact in the imaging data, wherein the near-field artifact comprises an artifact in the imaging data caused by the catheter body interfering with emission and reception of wave-based energy,
      (iii) identify an artifact area in the imaging data, the artifact area being a subset of the imaging data and corresponding to an area within an artifact distance from the imaging element and including an area outside of the catheter body,
      (iv) generate enhanced imaging data by reducing the near-field artifact from the imaging data by applying an artifact filter to the imaging data, wherein
         (A) the artifact filter comprises a circumferential filter and/or a radial filter, and
         (B) applying the artifact filter to the imaging data comprises applying the circumferential filter and/or the radial filter to only the imaging data in the identified artifact area, including imaging data outside of the catheter body and within the artifact area,
            wherein the enhanced imaging data comprises at least an enhanced first frame of imaging data and an enhanced second frame of imaging data, and wherein generating the enhanced imaging data comprises applying the artifact filter to the first frame of imaging data to generate the enhanced first frame of imaging data and applying the artifact filter to the second frame of imaging data to generate the enhanced second frame of imaging data; and
(v) generate an image from at least the enhanced first frame of imaging data and the enhanced second frame of imaging data.

2. The system of claim 1, wherein the imaging engine is adapted to detect the near-field artifact by identifying the near-field artifact and automatically determining the artifact area based on identification of the near-field artifact.

3. The system of claim 1, wherein the artifact filter is adapted to reduce the near-field artifact from imaging data associated with a blood-filled lumen.

4. The system of claim 1, wherein the artifact filter is adapted to reduce the near-field artifact from imaging data associated with a blood-cleared lumen.

5. The system of claim 1, wherein the artifact filter comprises a circumferential filter but does not comprise a radial filter.

6. The system of claim 1, wherein the artifact filter comprises a circumferential filter that is adapted to reduce the near-field artifact by filtering an arc associated with the near-field artifact from the imaging data.

7. The system of claim 1, wherein the artifact filter comprises a radial filter but does not comprise a circumferential filter.

8. The system of claim 1, wherein the artifact filter further comprises a spatial filter.

9. The system of claim 8, wherein the spatial filter comprises application of a low-pass filter to generate low-pass filtered image data, and wherein the low-pass filtered image data is subtracted out from the imaging data.

10. The system of claim 1, wherein the intravascular imaging device is an ultrasonic device.

11. The system of claim 1, wherein the intravascular imaging device is an optical coherence tomography device.

12. The system of claim 1, wherein the imaging engine is adapted execute a shader technique to reduce the near-field artifact from the imaging data, and wherein the shader technique includes a multi-pass application of a filter per data point.

13. The system of claim 1, wherein the near-field artifact in the imaging data corresponds to a body of the catheter assembly within which the intravascular imaging device is disposed.

14. A method for intravascular imaging comprising:
receiving imaging data from an intravascular imaging device, wherein the imaging data received from the intravascular imaging device comprises at least a first frame of imaging data and a second frame of imaging data, wherein the first frame of imaging data and the second frame of imaging data are not adjacent frames, wherein the first frame comprises a key frame, and wherein the second frame comprises a reference frame;
identifying an artifact area in the imaging data, the artifact area being a subset of the imaging data and corresponding to an area within an artifact distance of an imaging device used to acquire the imaging data;
detecting a near-field artifact in the artifact area of the imaging data, wherein the near-field artifact comprises an artifact in the imaging data caused by a catheter body interfering with emission and reception of wave-based energy;
generating enhanced imaging data by reducing the near-field artifact from the imaging data, the generating of the enhanced imaging data comprising applying an artifact filter to the imaging data, wherein the artifact filter comprises a circumferential filter and/or a radial filter, wherein applying the artifact filter to the imaging data comprises applying the circumferential filter and/or the radial filter to only imaging data in the identified artifact area wherein the enhanced imaging data comprises at least an enhanced first frame of imaging data and an enhanced second frame of imaging data, and wherein generating the enhanced imaging data comprises applying the artifact filter to the first frame of imaging data to generate the enhanced first frame of imaging data and applying the artifact filter to the second frame of imaging data to generate the enhanced second frame of imaging data; and
generating an image from at least the enhanced first frame of imaging data and the enhanced second frame of imaging data.

15. The method of claim 14, further comprising generating the imaging data by placing a catheter assembly including the intravascular imaging device in a vessel and imaging the vessel using an imaging element of the intravascular imaging device.

16. The method of claim 14, wherein detecting the near-field artifact comprises identifying the near-field artifact and automatically determining the artifact area based on identification of the near-field artifact.

17. The method of claim 14, wherein the artifact filter comprises a circumferential filter but does not comprise a radial filter.

18. The method of claim 14, wherein the artifact filter comprises a radial filter but does not comprise a circumferential filter.

19. The method of claim 14, wherein generating the enhanced imaging data comprises executing a shader technique to reduce the near-field artifact from the imaging data, and wherein executing the shader technique includes a multi-pass application of a filter per data point.

20. A system comprising:
(a) a catheter assembly including a catheter body and an intravascular imaging device within the catheter body and being adapted to generate imaging data, the intravascular imaging device including an imaging element;
(b) a processor; and
(c) a computer storage article storing program modules adapted to execute on the processor, the program modules comprising
(i) a receiving module adapted to receive the imaging data from the intravascular imaging device, wherein the imaging data received from the intravascular imaging device comprises at least a first frame of imaging data and a second frame of imaging data, wherein the first frame of imaging data and the second frame of imaging data are not adjacent frames, wherein the first frame comprises a key frame, and wherein the second frame comprises a reference frame,
(ii) a detection module adapted to
(A) identify an artifact area, the artifact area being a subset of the imaging data and corresponding to an area within an artifact distance of the imaging device and including an area outside of the catheter body, and
(B) detect a near-field artifact in the imaging data, wherein the near-field artifact comprises an artifact in the imaging data caused by the catheter body interfering with emission and reception of wave-based energy, (iii) an image processing module adapted to generate enhanced imaging data by reducing the near-field artifact from the imaging data by applying an artifact filter to the imaging data, the artifact filter including a circumferential filter and/or a radial filter that is applied to the imaging data only in the identified artifact area, including imaging data outside of the catheter body and within the artifact area, wherein the enhanced imaging data comprises at least an enhanced first frame of imaging data and an enhanced second frame of imaging data, and wherein generating the enhanced imaging data comprises applying the artifact filter to the first frame of imaging data to generate the enhanced first frame of imaging data and applying the artifact filter to the second frame of imaging data to generate the enhanced second frame of imaging data, and generate an image from at least the enhanced first frame of imaging data and the enhanced second frame of imaging data.

21. The system of claim 20, wherein identifying the artifact area comprises receiving a manually selected artifact area or recalling a predefined artifact area from memory.

\* \* \* \* \*